(12) United States Patent
Petter-Puchner et al.

(10) Patent No.: US 9,039,783 B2
(45) Date of Patent: May 26, 2015

(54) METHOD FOR THE IMPROVEMENT OF MESH IMPLANT BIOCOMPATIBILITY

(75) Inventors: Alexander Petter-Puchner, Vienna (AT); Heinz Redl, Vienna (AT)

(73) Assignees: Baxter International, Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 280 days.

(21) Appl. No.: 12/467,616

(22) Filed: May 18, 2009

(65) Prior Publication Data
US 2010/0292717 A1 Nov. 18, 2010

(51) Int. Cl.
A61F 2/02 (2006.01)
A61L 31/04 (2006.01)
A61F 2/00 (2006.01)
A61B 19/00 (2006.01)

(52) U.S. Cl.
CPC ........ *A61L 31/041* (2013.01); *A61B 2019/4884* (2013.01); *A61F 2/0063* (2013.01); *A61F 2/0077* (2013.01); *A61F 2002/009* (2013.01)

(58) Field of Classification Search
USPC ............ 606/215, 151, 214; 623/23.72, 23.75, 623/23.76; 600/29, 30, 37
See application file for complete search history.

(56) References Cited

U.S. PATENT DOCUMENTS

| | | | |
|---|---|---|---|
| 2,507,244 A | 5/1950 | Correll | |
| 2,558,395 A | 6/1951 | Studer | |
| 4,013,078 A | 3/1977 | Field | |
| 4,124,705 A | 11/1978 | Rothman et al. | |
| 4,164,559 A | 8/1979 | Miyata et al. | |
| 4,179,400 A | 12/1979 | Tsao et al. | |
| 4,265,233 A | 5/1981 | Sugitachi et al. | |
| 4,291,013 A | 9/1981 | Wahlig et al. | |
| 4,292,972 A | 10/1981 | Pawelchak et al. | |
| 4,298,598 A | 11/1981 | Schwarz et al. | |
| 4,300,494 A | 11/1981 | Graiff et al. | |
| 4,347,234 A | 8/1982 | Wahlig et al. | |
| 4,362,567 A | 12/1982 | Schwarz et al. | |
| 4,377,572 A | 3/1983 | Schwarz et al. | |
| 4,424,208 A | 1/1984 | Wallace et al. | |
| 4,453,939 A | 6/1984 | Zimmerman et al. | |
| 4,482,386 A | 11/1984 | Wittwer et al. | |
| 4,515,637 A | 5/1985 | Cioca | |
| 4,536,387 A | 8/1985 | Sakamoto et al. | |
| 4,540,410 A | 9/1985 | Wood et al. | |

(Continued)

FOREIGN PATENT DOCUMENTS

| | | |
|---|---|---|
| EP | 0132983 A | 2/1985 |
| EP | 0376931 | 7/1990 |

(Continued)

OTHER PUBLICATIONS

Ansell et al., "Gelfoam and Autologous Clot Embolization: Effect on Coagulation", *Invest. Radiol.* (1978) 13:115-120.

(Continued)

*Primary Examiner* — Gregory Anderson
*Assistant Examiner* — Christina Lauer
(74) *Attorney, Agent, or Firm* — Kilpatrick Townsend & Stockton LLP (57) ABSTRACT

The present invention provides a method of fixating a mesh implant to a tissue of a subject comprising attaching said mesh implant to said tissue, covering said mesh implant by an antiadhesive barrier, wherein said antiadhesive barrier is attached to said mesh implant by a biocompatible adhesive.

18 Claims, 3 Drawing Sheets

(56) References Cited

U.S. PATENT DOCUMENTS

| | | |
|---|---|---|
| 4,543,332 A | 9/1985 | Jao et al. |
| 4,554,156 A | 11/1985 | Fischer et al. |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,891,359 A | 1/1990 | Saferstein et al. |
| 4,925,677 A | 5/1990 | Feijen |
| 4,946,870 A | 8/1990 | Partain, III. et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,853,749 A | 12/1998 | Hobbs |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,386 B1 | 10/2002 | Schacht et al. |
| 6,458,889 B1 | 10/2002 | Trollsas |
| 6,624,245 B2 | 9/2003 | Wallace et al. |
| 6,706,690 B2 | 3/2004 | Reich et al. |
| 6,884,232 B1 * | 4/2005 | Hagmann et al. ............... 604/82 |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 2002/0193448 A1 | 12/2002 | Wallace et al. |
| 2003/0064109 A1 | 4/2003 | Qian et al. |
| 2004/0063613 A1 * | 4/2004 | Rolke et al. ..................... 514/2 |
| 2004/0172048 A1 * | 9/2004 | Browning ................... 606/151 |
| 2005/0261782 A1 * | 11/2005 | Hoganson ................ 623/23.74 |
| 2006/0147492 A1 * | 7/2006 | Hunter et al. ................. 424/426 |
| 2006/0167561 A1 | 7/2006 | Odar et al. |
| 2007/0111937 A1 * | 5/2007 | Pickar et al. ................... 514/12 |
| 2008/0085316 A1 | 4/2008 | Qian et al. |
| 2008/0091277 A1 * | 4/2008 | Deusch et al. ............ 623/23.74 |
| 2008/0286376 A1 | 11/2008 | Qian et al. |
| 2009/0142396 A1 | 6/2009 | Odar et al. |
| 2009/0259251 A1 * | 10/2009 | Cohen .......................... 606/228 |
| 2010/0028309 A1 | 2/2010 | Odar et al. |
| 2010/0318048 A1 | 12/2010 | Hoefinghoff et al. |

FOREIGN PATENT DOCUMENTS

| | | |
|---|---|---|
| EP | 0132983 B2 | 6/1991 |
| EP | 0493387 | 7/1992 |
| EP | 0891193 | 1/1999 |
| EP | 0612252 B1 | 12/1999 |
| EP | 1084720 A1 | 3/2001 |
| EP | 1283063 A1 | 2/2003 |
| EP | 1484070 A1 | 12/2004 |
| EP | 01414370 B1 | 4/2007 |
| JP | 59-113889 | 6/1984 |
| JP | 05308969 | 11/1993 |
| JP | 6-254148 | 9/1994 |
| JP | 9-504719 | 5/1997 |
| JP | 07090241 | 4/2007 |
| KR | 10-1991-007847 B1 | 10/1991 |
| WO | WO 86/00912 | 2/1986 |
| WO | WO 92/21354 | 12/1992 |
| WO | WO 94/27630 A1 | 12/1994 |
| WO | WO 95/12371 | 5/1995 |
| WO | WO 92/22252 | 6/1995 |
| WO | WO 95/15747 | 6/1995 |
| WO | WO 96/04025 | 2/1996 |
| WO | WO 96/06883 | 3/1996 |
| WO | WO 96/10374 | 4/1996 |
| WO | WO 96/10428 | 4/1996 |
| WO | WO 96/14368 | 5/1996 |
| WO | WO 96/39159 | 12/1996 |
| WO | WO 97/37694 A1 | 10/1997 |
| WO | WO 98/08550 A1 | 3/1998 |
| WO | WO 99/13902 A1 | 3/1999 |
| WO | WO 02/22184 A2 | 3/2002 |
| WO | WO 02-070594 A2 | 9/2002 |
| WO | WO 03/0007845 A1 | 1/2003 |
| WO | WO 2004/108179 A1 | 12/2004 |
| WO | WO 2006/031358 A | 3/2006 |
| WO | WO 2006/118460 A1 | 11/2006 |

(56) References Cited

FOREIGN PATENT DOCUMENTS

| WO | WO 2007/001926 A2 | 1/2007 |
|---|---|---|
| WO | WO 2007/137839 A2 | 12/2007 |
| WO | WO 2007/137839 A3 | 12/2007 |
| WO | WO 2008/016983 A2 | 2/2008 |

OTHER PUBLICATIONS

Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).
Barton et al., "Fibrin Glue as a Biologic Vascular Patch—A Comparative Study" (abstract posted at http://www.ncbi.nlm.nih.gov/ on Jan. 3, 2001 from) J. Surg. Res. (1986) 40(5): 510-513.
Baxter product brochure for TissuFleece E, TissuCone E and TissuFoil E (2003).
Baxter Product Catalogue; Collagen; 4 pages (2006).
Boyers et al., "Reduction of Postoperative Pelvic Adhesions in the Rabbit with Gore-Tex Surguical Membrane" Fert. Ster. (1988) 49(6):1066-1070.
Bruck, S. D., Ed., Controlled Drug Delivery, CRC Press, Boca Raton, FL (1983) A title page and table of contents.
Cantor et al., "Gelfoam and Thrombin in Gastrointestinal Bleeding: An Experimental Study", pp. 890-893.
Cantor et al., "Gelfoam and Thrombin in Treatment of Massive Gastroduodenal Hemmorhage: A Preliminary Report" Am J. Surg. (1950) pp. 883-887.
Cantor et al., "Gelfoam and Thrombin in Treatment of Massive Upper Gastroduodenal Hemorrhage", Am. J. Surg. (1951) pp. 230-235.
Chaplin, J.M., et al.; "Use of an Acellular Dermal Allograft for Dural Replacement: An Experimental Study"; Neurosurgery: vol. 45:2; pp. 320-327 (Aug. 1999).
Chuang et al., "Sheath Needle for Liver Biopsy in High-Risk Patients", Radiology(1988) 166:261-262.
Collins et al., "Enemata of Gelfoam-Milk Suspension Combined with Thrombin Solution to Control Massive Hemorrhage Following Anorectal Surgery", Am. J. Proctol. (1951) 2:60-63.
Collins, Ronald et al., "Use of Collagen Film as a Dural Substitute: Preliminary Animal Studies", Journal of Biomedical Materials Research, vol. 25, 267-276 (1991).
Edgerton et al., "Vascular Hamartomas and Hemangiomos: Classification and Treatment" Southern Med. J. (1982) 75(12):1541-1547.
Filippi, R., et al.; "Bovine Pericardium for Duraplasty: Clinical Results in 32 Patients"; Neurosurg. Rev.; vol. 20; pp. 103-107 (2001).
GentaFleece Kollagenvlies Version 5 found on internet at: http://www.advancingbiosurgery.com/en_EU/downloads/ifu_gentafleece.pdf, Mar. 2002, 2 pages.
Heller et al., "Release of Norethindrone from Poly(Ortho Esters)" Polymer Engineering Sci. (1981) 21:727-731.
Hieb, Lee D. et al., "Spontaneous Postoperative Cerebrospinal Fluid Leaks Following Application of Anti-Adhesion Barrier Gel", SPINE vol. 26, No. 7, pp. 748-751, 2001.
Hood et al., "Efficacy of Topical Hemostat Floseal Matrix in Vascular Surgery," 24th World Congress of the International Society for Cardiovascular Surgery (Sep. 12-16, 1999), 2 pages total.
Hotz et al., "Collagen and Fibrin as Biologic Binders from Granular Hydroxyapatite" (abstract posted at http://www.ncbi.nlm.nih.gov/ on Jan. 3, 2001 from) Dtsh. Z. Mund. Kiefer Geichtshir. (1989) 13(4):296-300.
Jeong et al., "Biodegradable Block Copolymers as Injectible Drig-Delivery Systems" Nature (1997) 388:860-862.
Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.
Kline, D.G.; "Dural Replacement with Resorbable Collagen"; Arch Surg; vol. 91; pp. 924-929 (Dec. 1965).
Knopp U., "A new collagen foil versus a cadaveric dura graft for dural defects—a comparative animal experimental study", EANS—12th European Congress of Neurosurgery, Lisbon, Sep. 7-12, 2003, 663-666.

Krill et al., "Topical Thrombin and Powdered Gelfoam: An Efficiaent Hemostatic Treatment for Surgery", J. Tenn. Dent. Assoc . (1986) 66(2):26-27.
Kuhn, J. et al., "Bilateral Subdural Haemotomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.
Langer et al., "Chemical and Physical Structure of Polymerns as Carriers for Controlled Release of Bioactive Agents: A Review" Rev. Marco Chem. Phys. (1983) C23(1):61-126.
Laquerriere, A., et al.; "Experimental Evaluation of Bilayered Human Collagen as a Dural Substitute"; J. Neurosurg; vol. 78; pp. 487-491 (Mar. 1993).
Le, Anh X. et al., "Unrecognized Durotomy After Lumbar Discectomy: A Report of Four Cases Associated with the Use of ADCON-L", SPINE vol. 26, No. 1, pp. 115-118, 2001.
Lee, J.F., et al.; "Experimental Evaluation of Silicone-Coated Dacron and Collagen Fabric-Film Laminate as Dural Substitutes"; J. Neurosurg.; vol. 27; pp. 558-564 (Apr. 1967).
Leong et al., "Polyanhydrides for Controlled Release of Bioactive Agents" Biomaterials (1986) 7:364-371.
Leong et al., "Polymeric Controlled Drug Delivery" Adv. Drug Delivery Rev. (1987)1:199-233.
Maok, "Hemostatic Agents" (1991) Today's O.R. Nurse, pp. 6-10.
Masar et al., "Synthesis of Polyurethanes and Investigation of their Hydrolytic Stability" J. Polymer. Sci., Polymer Symposium (1979) 66:259-268.
Matsumoto, K., et al.; "A Gelatin Coated Collagen-Polyglycolic Acid Composite Membrane as a Dural Substitute"; ASAIO Journal; pp. 641-645 (2001).
Maurer, P.K., et al.; "Vicryl (Polyglactin 910) Mesh as a Dural Substitute"; J Neurosurg; vol. 63; pp. 448-452 (Sep. 1985).
McClure et al., "Massive Gastroduodenal Hemorrhage: Treatment with Powdered Gelfoam and Buffered Thrombin Solution" Surg. (1952) 32:630-637.
Meddings, N., et al.; "Collagen Vicryl—A New Dural Prosthesis"; Acta Neurochir; vol. 117; pp. 53-58 (1992).
Mello, L.R., et al.; "Duraplasty with Biosynthetic Cellulose: An Experimental Study"; J Neurosurg; vol. 86; pp. 143-150 (Jan. 1997).
Narotam, P.K., et al.; "A Clinicopathological Study of Collagen Sponge as a Dural Graft in Neurosurgery"; J Neurosurg; vol. 82; pp. 406-412 (Mar. 1995).
Narotam, P.K., et al.; "Experimental Evaluation of Collagen Sponge as a Dural Graft"; British Journal of Neurosurgery; vol. 7; pp. 635-641 (1993).
O'Neill, P., et al.; "Use ofPorcine Dermis as Dural Substitute in 72 Patients"; J. Neurosurg.; vol. 61; pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; Acta Neurochir; vol. 139; pp. 827-838 (1997).
Park, Y-K., at al.; "Prevention ofArachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
PCT International Preliminary Report on Patentability and Written Opinion mailed Feb. 17, 2009, International Application No. PCT/US2007/074984, 8 pages.
Pietrucha, K.; "New Collagen Implant as Dural Substitute"; Biomatarials; vol. 12; pp. 320-323 (Apr. 1991).
Pitt et al., "Controlled Release of Bioactive Materials", R. Baker, Ed., Academic Press, New York, 1980.
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al., "Utilisation du Polyester Urethane (NEURO-PATCH®) Comme Substitut Dural"; Neurochirugie; vol. 49:2-3; pp. 83-89 (2003), English abstract only on p. 83.

(56) References Cited

OTHER PUBLICATIONS

Raul, J.S., et al.; "Utilisation du Polyester Urethane (NEUROPATCH®) Comme Substitut Dural"; Neurochirugie; vol. 49:2-3; pp. 83-89 (2003).
Reddy, M., et al.; "A Clinical Study of a Fibrinogen-Based Collagen Fleece for Dural Repair in Neurosurgery"; Acta Neurochir; vol. 144; pp. 265-269 (2002).
Riley et al., "Percutaneous Liver Biopsy with Plugging of Needle Track: A Safe Method for Use in Patients with Impaired Coagulation" *Lancet* (Aug. 25, 1984) pp. 436.
Ross, Jeffrey S. et al., "Association Between Peridural Scar and Recurrent Radicular Pain After Lumbar Discectomy: Magnetic Resonance Evaluation", Neurosurgery, pp. 855-863, 1996.
San-Galli, F., et al.; "Experimental Evaluation of a Collagen-Coated Vicryl Mesh as a Dural Substitute"; Neurosurgery: vol. 30:3; pp. 396-401 (1992).
Shaffrey, C.I., et al.; "Neurosurgical Applications of Fibrin Glue: Augmentation of Dural Closure in 134 Patients"; Neurosurgery; vol. 26:2; pp. 207-210 (1990).
Sidman et al., "Biodegradable, Implantable Sustained Release Systems Based on Glutamic Acid Copolymers" *J. Membrane Science* (1979) 7:227-291.
Smith, KA, et al.; "Delayed Postoperative Tethering of the Cervical Spinal Corei"; J Neurosurg; vol. 81; pp. 196-201 (Aug. 1994).
Springorum, H.W.; "Die Verwendung von Kollagenfolien zur Uberbruckung von Defekten des Gleitgewebes bei Achillotenotomien und Achillessehnenrupturen"; Akt. Traumata!.; vol. 15; pp. 120-121 (1985), *English abstract only on p. 120.*
Springorum, H.W.; "Die Verwendung von Kollagenfolien zur Uberbruckung von Defekten des Gleitgewebes bei Achillotenotomien und Achillessehnenrupturen"; Akt. Traumata!.; vol. 15; pp. 120-121 (1985).
Stricker, A., et al.; "Die Verwendung von TissuFoil Membran bei der Sinusbodenaugmentation"; Ellipse; vol. 17:1; pp. 1-5 (2001), *English abstract only on p. 1.*
Stricker, A., et al.; "Die Verwendung von TissuFoil Membran bei der Sinusbodenaugmentation"; Ellipse; vol. 17:1; pp. 1-5 (2001).
Sugitachi et al., "A Newly Devised Chemo-embolic Agent, G.T. XIII-ADM." (English abstract posted at http://www.ncbi.nlm.nih.gov/ on Jan. 3, 2001 from) *Gan. To. Kagaku Ryoho.* (1985) 12(10) 1942-1943.
Sugitachi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho.* (1992) 19(10):1640-1643.
Sugitachi et al., "Preoperative Transcatheter Arterial Chemoembolization for Locally Advanced Breast Cancer: Application for New Thrombotic Materials" *Japan J. Surg.* (1983) 13(5):456-458.
T. Kofidis et al., "Clinically established Hemostatis Scaffold (Tissue Fleece) as Biomatrix in Tissue- and organ-engineering research", Tissue Eng vol. 9, No. 3, 2003, S.517-523; ISSN: 1076-3279.
TissuFleece E found on internet at: http://www.biosurgery.de/Produkte/pdf/TissuFleece-E_GI.pdf, Feb. 2003, 2 pages.
Tobin et al., "Plugged Liver Biopsy in Patients with Impaired Coagulation" *Digestive Diseases and Science* (1989) 34(1):13-15.
Tucker et al., "Absorbable Gelatin (Gelfoam) Sponge" Charles T. Thomas, Publisher, Springfiled, Illinois, 3-125.
Vander Salm et al., "Reduction of Sternal Infection by Application of Topical Vancomycin" *J. Thorac. Surg.* (1989) 98:618-622.
Vinas, F.E., et al.; "Evaluation of Expanded Polytetrafluoroethylene (ePTFE) versus Polydioxanone (PDS) for the Repair of Dura Mater Defects"; Neurological Research; vol. 21; pp. 262-268 (Apr. 1999).
Warren, W.L., et al.; "Dural Repair Using Acellular Human Dermis: Experience with 200 Cases: Technique Assessment"; Neurosurgery; vol. 46:6; pp. 1391-1396 (Jun. 2000).
Yuki et al., "Effects of Endoscopic Variceal Sclerotherapy using GT XIII on Blood Coagulation Tests and the Renal Kallikrein-kinin System" (English abstract posted at http://www.ncbi.nlm.nih.gov/ on Jan. 3, 2001 from) *Gastroentral. Japan* (1990) 25(5):561-567.
Ziegelaar, B.W.; "Tissue Engineering of a Tracheal Equivalent", Doctoral Thesis at Ludwig Maximilians University, Munich, Germany; 25 pages (2004).
Ziegelaar, BW et al., "The characterisation of human respiratory epithelial cells cultured on reabsorbable scaffolds: first steps towards a tissue engineered tracheal replacement", Biomaterials 23 (2002), 1425-1438; ISSN 0142-9612.
Zins et al., "US-Guided Percutaneous Liver Biopsy with Plugging of the Needle Track: A Prospective Study in 72 High-Rish Patients" *Radiology* (1992) 184(3):841-843.
Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.
Jonas, Richard A., et al., "A new sealant for knitted Dacron prostheses: Minimally cross-linked gelatin", J. Vasc. Surg., Mar. 1988;7(3), pp. 414-419.
Larson, Paul O., "Topical Hemostatic Agents for Dermatologic Surgery", J. Dermatol. Surg. Oncol., Jun. 1988;14(6), pp. 623-632.
McPherson, J. M. et al., "An examination of the biologic response to injectable, glutaraldehyde cross-linked collagen implants", J. Biomed. Mater. Res., Jan. 1986;20(1), pp. 93-107.
McPherson, J. M., et al., "The preparation and physiochemical characterization of an injectable form of reconstituted, glutaraldehyde cross-linked, bovine corium collagen", J. Biomed. Mater. Res., Jan. 1986; 20(1), pp. 79-92.
McPherson, John M., et al., "The Effects of Heparin on the Physiochemical Properties of Reconstituted Collagen", Coll. Relat. Res., Jan. 1988;8(1), pp. 65-82.
Nimni, M. E., et al., "Chemically modified collagen: A natural biomaterial for tissue replacement", J. Biomed. Mater. Res., Jun. 1987;21(6), pp. 741-771.
Nimni, Marcel E., "The cross-linking and structure modification of the collagen matrix in the design of cardiovascular prosthesis", J. of Cardiac Surgery, Dec. 1988;3(4), pp. 523-533.
Rosenblatt, Joel, et al., "Effect of electrostatic forces on the dynamic rheological properties of injectable collagen biomaterials", Biomaterials, 1992;13(12), pp. 878-886.
Rosenblatt, Joel, et al., "Injectable collagen as a pH-sensitive hydrogel", Biomaterials, Oct. 1994;15(12), pp. 985-995.
Rossler, B., et al., "Collagen microparticles: preparation and properties", J. Microencapsulation, 1995, Jan.-Feb.;12(1), pp. 49-57.
Wallace, Donald G., et al., "Injectable cross-linked collagen with improved flow properties", J. of Biomedical Materials Research, Aug. 1989;23(8), pp. 931-945.
Wallace, Donald, "The relative contribution of electrostatic interactions to stabilization of collagen fibrils", Biopolymers, May-Jun. 1990; 29(6-7), pp. 1015-1026.

\* cited by examiner

METHOD FOR THE IMPROVEMENT OF MESH IMPLANT BIOCOMPATIBILITY

FIELD OF THE INVENTION

The present invention relates to the field of surgery, in particular the integration of artificial mesh implants.

BACKGROUND OF THE INVENTION

The placement of synthetic meshes into the body of a patient has become routine in the field of surgical practice. The most common use for mesh implants is the placement into the abdominal cavity for the repair of ventral and incisional hernias. The meshes are either placed extraperitoneally in onlay or sublay technique or intraperitoneally in intraperitoneal onlay mesh technique (IPOM). Inlay technique also played a role in the past. IPOM technique is indicated in multiple defect hernias (also known as Swiss cheese hernias) as well as for the treatment of large abdominal wall defects with loss of domain in obese patients. The implants are usually fixed by sutures, tacks or anchors. Complications found with IPOM technique are seroma formation, impaired functionality of the abdominal wall, chronic pain and adhesion formation. Chronic pain (continuous or intermittent pain persisting for more than 3 months postoperatively is mainly caused by perforating fixation devices with a reported incidence of 5-15% in open and laparoscopic hernia repair operations.

Clinical and experimental studies have shown that synthetic meshes as well as fixation devices can evoke a foreign body reaction. Unspecific tissue inflammation provokes tissue adhesions often elicited by protruding tacks, sutures or sharp mesh margins. These adhesions are potentially resulting in major complications like bowel adhesion, bowel obstruction or perforation.

Different mesh concepts for adhesion prevention have been developed including coated meshes, developed for separation of peritoneal defects and used for the individual coating of meshes. Large pores and high flexibility increase mesh integration into the abdominal wall and provide good biomechanical function. Examples for coated meshes are Parietex Composite®, Sepramesh® and Proceed®. The idea of integrating mesh and antiadhesive layer in the implant is to separate implant and viscera until the mesh is covered by neomesothelium (after approximately 10 days) and in the following to reduce the foreign body reaction and adhesion formation triggered by the implant.

However, using coated meshes may still trigger adverse reaction due to the use of mechanical fixation means such as sutures, tacks and anchors, which may extend from the implant. It is therefore a goal of the present invention to provide improved means to prevent or minimize all causes of unwanted tissue adhesion to the implant or its fixtures.

SUMMARY OF THE INVENTION

In a first aspect the present invention provides a method of fixating a mesh implant to a tissue of a subject comprising attaching said mesh implant to said tissue, covering said mesh implant by an antiadhesive barrier, wherein said antiadhesive barrier is attached to said mesh implant by a biocompatible adhesive.

The invention also relates to a method of reducing the risk of adhesion formation after surgery to a mesh implant in a subject comprising attaching said mesh implant to a tissue of the subject and covering said mesh implant by an antiadhesive barrier, whereby this risk is reduced. The mesh implant may be attached to the tissue by a mechanical fixation device. In this case, the antiadhesive barrier may also cover said mechanical fixation device.

Furthermore the invention relates to a mesh implant, antiadhesive barrier and a biocompatible adhesive, respectively, for use in the inventive method. According to this aspect the invention also provides the use of a mesh implant or antiadhesive barrier for the manufacture of a surgical device for the inventive methods, as well as the use of the biocompatible adhesive for the manufacture of a pharmaceutical preparation for the inventive methods.

In another aspect the invention relates to a kit comprising an antiadhesive barrier and a biocompatible adhesive, optionally a mesh implant, and instructions for its use. The kit may be used for any inventive method including the method of fixating a mesh implant to a tissue of a subject comprising attaching said mesh implant to said tissue, covering said mesh implant by an antiadhesive barrier, wherein said antiadhesive barrier is attached to said mesh implant by a biocompatible adhesive, and instructions for said method.

BRIEF DESCRIPTION OF THE DRAWINGS

FIG. 1A shows an embodiment of the present invention. A surface 105 such as a peritoneal surface can include an injury 110 such as a hernia. A mesh implant 115 can be applied to the injury 110 and then covered with an antiadhesion barrier 120.

FIG. 1B shows another embodiment of the present invention. A surface 105 such as a peritoneal surface can include an injury 110 such as a hernia. A mesh implant 115 can be applied to the injury 110 and then covered with an antiadhesion barrier 120. The mesh implant 115 is attached with a mechanical fixation device 125, and the antiadhesion barrier 120 covers the mechanical fixation device 125 as well as the mesh implant 115.

DETAILED DESCRIPTION OF THE INVENTION

Figure 1A:
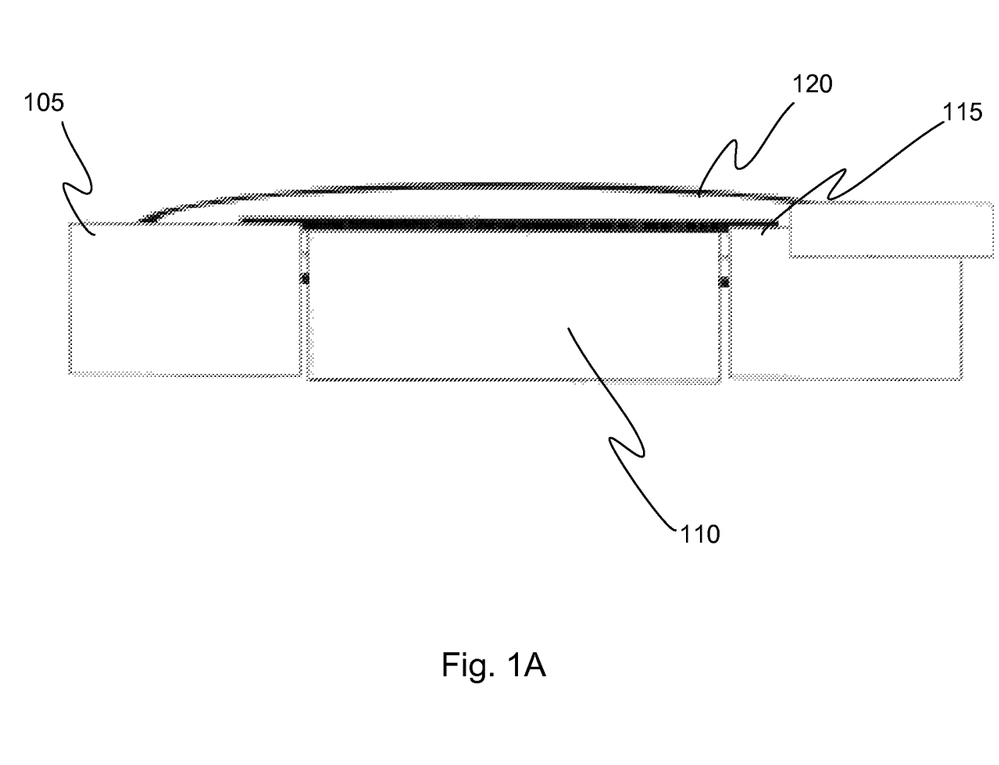
Figure 1B:
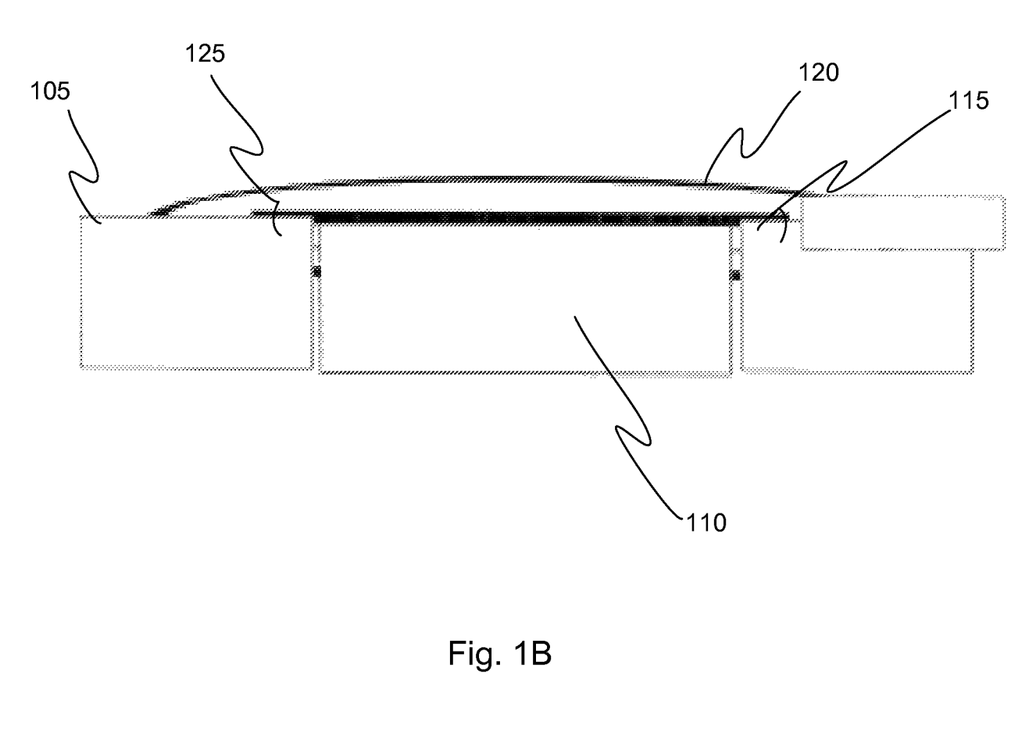
Figure 2:
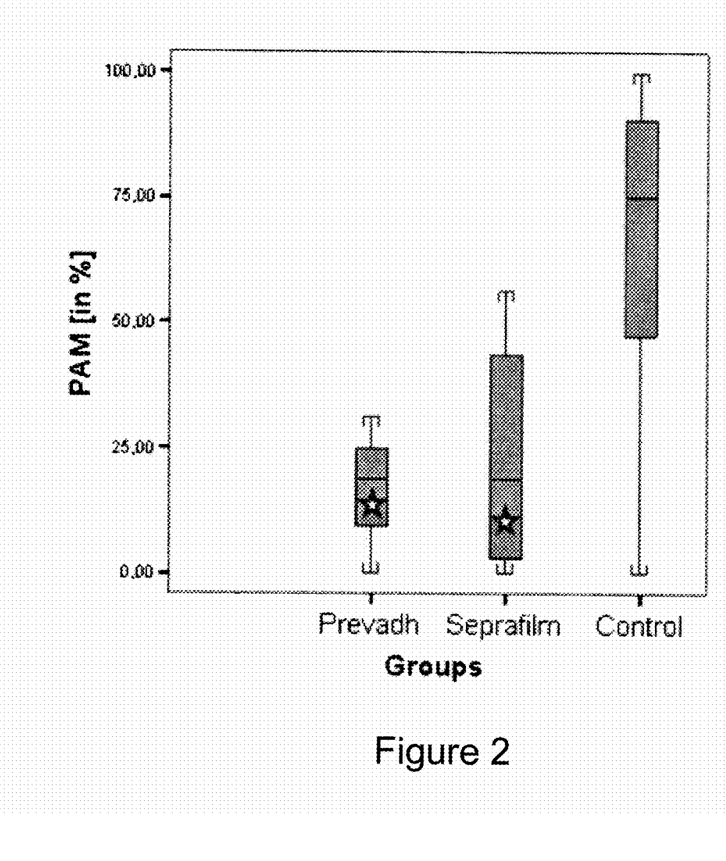
FIG. 2 shows boxplots of percental adhesion-coverage of mesh surface in all groups. Adhesion-covered mesh surface differs within the three groups (p=0.0017). It could be shown that Control group is statistically different from Prevadh group (p=0.0035) and from Seprafilm group (p=0.0120). Groups significantly different from Control group are marked by a star.

One object of the invention is to increase biocompatibility of mesh implants, in particular by reducing and minimizing adhesion formation during surgical recovery. Industry supplies various kinds of anti-adhesive barriers which can be inserted into the abdominal cavity separately and then cover regenerating tissue or implants in general. This approach has yet gained no acceptance for the fixation of mesh implants, mostly because of the technical difficulties to fixate the barriers to the mostly porous meshes. The use of any perforating tool for the purpose of attaching the anti-adhesive barrier to the mesh would contradict the desired advantage of creating one smooth anti-adhesive layer. Adhesives or glues surprisingly proved to be excellent agents to fixate antiadhesive barriers to the mesh and cover underlying fixation devices because it allows three dimensional sealing, a reduction of dead space between peritoneum and anti-adhesive barrier (leading to a reduced incidence of seromas) and can also be used to reduce the number of fixation devices as well (if used to fixate the mesh implant itself onto the tissue surface). A smaller number of tacks and sutures translates to a decreased risk of perforating nerves, vessels or bowel, eventually reducing the risk of complications.

Thus, the present invention provides a method of fixating a mesh implant to a tissue of a subject comprising attaching the mesh implant to said tissue, covering the mesh implant by an antiadhesive barrier, wherein the antiadhesive barrier is attached to the mesh implant by a biocompatible adhesive. Attaching the antiadhesive barrier onto the mesh results in an increased biocompatibility and reduced the risk of postoperative adhesion formation. Therefore, also provided is a method of reducing the risk of adhesion formation after surgery to a mesh implant in a subject comprising attaching the mesh implant to a tissue of the subject and covering the mesh implant by an antiadhesive barrier, whereby the risk is reduced. As those skilled in the art can readily recognize, all preferred or further embodiments can be read on both methods which are easily combinable.

Antiadhesive barriers prevent direct contact of the mesh and intraperitoneal organs. Combining one type of mesh with a different antiadhesive barrier providing a barrier between implant and any opposing tissues until the mesh is covered by neomesothelium, prevents further complications. Contrary to the antiadhesive barrier, the mesh implant remains at the site and may eventually integrate into the tissue onto which it is fixed. This fixation can be by any known means including using mechanical fixation by sutures. Antiadhesive barriers can be fixed to the mesh in a new atraumatic way by the use of the bioresorbable adhesive, e.g. slow clotting fibrin sealant.

The "mesh implant" is a prosthesis to be attached to a tissue. It is preferably biocompatible to the subject, does usually not provoke an immune response and is suitable for integration. Usually such a mesh implant is of a flexible polymer used to physically strengthen the tissue. Mesh implants are generally known in the art, e.g. in the WO 2006/102477, and are commercially available such as Vitamesh® (Proxy Biomedics, Ireland), a polypropylene mesh. Further mesh materials include polyesters, and polytetrafluoroethylene (PTFE). In its fixed state one side of the mesh implant will face the tissue and another side the antiadhesive barrier (to prevent adhesion formation on this side of the mesh). A mesh is usually in form of a porous sheet or foil, in particular of a woven structure. It may have pore sizes of 0.1 mm up to 15 mm.

The "mesh implant" includes meshes as available on the market as well as so called "self adhesive" meshes, e.g. including an adhesive on the mesh itself.

"Antiadhesive barrier" as used herein refers to a sheet material which does not provoke or limit adhesion formation with regenerating tissue. It is usually continuous, laminar or non-porous. The antiadhesive barrier, synonymous with antiadhesive layer or antiadhesive foil, may be in contact to nearby organs but shall remain unattached after surgery, including the 5-10 day postoperative period in which adhesions usually form (of course, only if not artificially attached). One side will face the mesh implant and its opposing side faces away from the tissue into any body cavity or any interior or exterior space depending on the tissue type. In order to completely cover the mesh implant, the borders of the antiadhesive barrier can be fixed or sealed to the same tissue onto which the mesh implant is fixed. In order to avoid unnecessary irritants and corners on the barrier, it might be provided in form of a single sheet. Commercially available antiadhesive barriers include SurgiWrap® (Mast Biosurgery, USA)—an amorphous bioresorbable copolymer of 70:30 poly(L-lactide-co-D,L-lactide), Prevadh® (Covidien, USA)—a hydrophilic smooth and continuous film of a hemostatic collagen sponge, one side being of smooth and non-porous bovine oxidized type-1 atelocollagen, and Seprafilm® (Genzyme, USA)—a negatively charged polymer of hyaluronate and carboxymethylcellulose.

The antiadhesive barrier may be a foil or membrane in order to allow coverage of the mesh implant. In this case, the antiadhesive barrier may be slightly larger than the mesh implant.

The antiadhesive barrier can be bioresorbable to allow automatic removal after the mesh implant has integrated into the tissue and no further protection from adhesion formation is necessary.

The bioresorbability can be between 4 and 60 days, in general the barrier can be fully resorbed after 4 days, after 7 days, after 14 days or more. In further embodiments the bioresorption can take up to 6 months, up to 2 months, up to 8 weeks or up to 20 days. For example the antiadhesive barrier may comprise a biopolymer, a polysaccharide, e.g. a negatively charged polysaccharide, hyaluronic acid, cellulose, a cellulose derivative, such as e.g. methylcellulose, carboxymethylcellulose, oxidized cellulose or oxidized regenerated cellulose; polylactic acid (PLA), poly(L-lactide-co-D,L-lactide), type-1 atelocollagen, collagen, poly(lactic-co-glycolic acid) (PLG), polyglactin or mixtures thereof or a natural biologic membrane like amnion, small intestinal submucosa, skin (including processed skin) or mixtures thereof or a non-resorbable biocompatible membrane, e.g. polytetrafluoroethylene.

The main purpose of the antiadhesive barrier is to cover the mesh implant so that the side of the mesh implant facing away from the tissue onto which it is fixed (e.g. also any mechanical fixation devices) is (are) not exposed to any other tissues, optionally also other body fluids, during the period of adhesion formation, usually 5-10 days after a surgical operation. To this purpose the antiadhesive barrier can also be tightly sealed to the tissue onto which the mesh implant is fixed to reduce the risk of any further ingrowth into any possible gaps. The possibility of tightly sealing the antiadhesive barrier is a particular advantageous aspect of the use of the inventive biocompatible adhesive. Of course, it shall be understood that the biocompatible adhesive might be degraded and the covered or sealed state of the implant is not the permanent state to be achieved but only the protection during the regenerative processes.

The "biocompatible adhesive", also referred to as biocompatible glue, is a material that is applied to two surfaces for attachment. It is usually applied in fluid state and solidifies to a solid or semi-solid (including gel) state for attachment. The biocompatible adhesive should not be confused with any adhesives naturally formed by the subjects body, e.g. in response to surgery. These naturally forming adhesives shall remain detached from the antiadhesive barrier whereas the biocompatible adhesive is a material that is artificially used to adhere the antiadhesive barrier to the mesh implant—or alternatively or additionally to the tissue onto which the mesh is fixed (e.g. the antiadhesive barrier can envelope the mesh implant on one side). The biocompatible adhesive can be any compound that is compatible or biologically acceptable to the subject and may not provoke an immune response. Such biocompatible adhesives can be biopolymers that may be applied as polymer-precursors that can be induced to polymerize in situ. If mechanical means are included then preferably no protrusions extend through the antiadhesive barrier onto the opposing side to the mesh facing side.

The biocompatible adhesive may be provided as such, or present on a foil or on a mesh implant.

The biocompatible adhesive may comprise at least two components, which are either premixed and applied or mixed upon application. Upon mixture of the component, the solidification process initiates. If premixed the adhesive usually stay in the fluid state long enough to allow its application onto to surgical site. In another embodiment the sealant components are preapplied to the barrier, which upon contact with tissue will react and seal (=selfadherent barrier). The biocompatible adhesive may comprise natural polymers or polymerizable compounds, in particular such as fibrinogen and/or thrombin. One possible type of adhesives are fibrin sealants, which can fixate the antiadhesive barrier due to a clotting reaction. Examples of a suitable fibrin sealant are Tissucol® or Artiss® (Baxter Biosciences, Vienna). Depending on the type of operation, fast or slow clotting fibrin sealants can be used. For longer surgical adaptions usually slow clotting sealants are used. The biocompatible adhesives can be bioresorbable (or biologically degradable). Adhesions generally form seven to ten days postoperatively. After its main function, holding the antiadhesive barrier in place long enough until this phase passes, the biocompatible adhesive may be removed by natural body function. Thus adhesives may be used which are removed (or biodegraded) e.g. after 4 days, after 7 days, after 14 days or more. In further embodiments the removal or bioresorption can take up to 6 months, up to 6 weeks, up to 25 days or up to 20 days. The subject may be any (nonhuman) animal or a human with a potential requirement for a mesh implant. In some embodiments said subject is a vertebrate. Furthermore, the subject may be a bird or a mammal, in particular selected from primates, horse, cow, camel, dog, cat, sheep, goat, rodents, including rat, mouse, hamster, rabbit.

The tissue might be any tissue that needs physical strength or support. Such a tissue might be e.g. lining of a body cavity, in special embodiments the tissue can be a member of the abdominal wall of said subject. The mesh implant shall have a tensile strength sufficient to support a given tissue. E.g. for the abdominal wall of a human tensile strengths may be required to resist 150 mm Hg (the intra-abdominal pressure during coughing). Possible tensile strengths can be to withstand 100 mm Hg, 150 mm Hg, 200 mm Hg, 250 mm Hg depending on the subject and tissue. The abdominal wall comprises different layers, including the peritoneum, the fascia transversalis, muscle tissue and an outer layer of fascia onto which the mesh implant might be fixed. In special embodiments the mesh implant is fixed to the ventral side of the tissue. E.g. the mesh implant can be placed intraperitoneal.

Usually such a mesh implant is used to treat an injury of the tissue such as a rupture. The mesh implant can cover this injury or rupture in order to prevent any adverse reactions such as a protrusion of tissue through the rupture. Such a rupture might be in any possible tissue, e.g. of the abdominal wall, such as a muscle tissue or in a membrane.

The treated condition, e.g. the injury, of the tissue can be a hernia. Examples of hernias are umbilical hernias—resulting in a protrusion of intraabdominal contents through a weakness at the site of passage of the umbilical cord through the abdominal wall—and incisional hernias, which might be a defect as a result of an incompletely healed surgical wound, such as after median laparotomy (ventral hernias). Other types of hernias are inguinal hernia, femoral hernia, diaphragmatic hernia, epigastric hernia, lumbar hernia, Littre's hernia, obturator hernia, paraumbilical hernia, perineal hernia, properitoneal hernia, Richter's hernia, sliding hernia, sciatic hernia, spigelian hernia, sports hernia, Velpeau hernia and spinal disc hernia. The present invention provides a method to minimize and even prevent adhesion formation after intraperitoneal onlay placement of hernia meshes by covering the mesh with a localized antiadhesive barrier. The barrier can be a preformed antiadhesive foil to be fixed to hernia meshes without the need of mechanical fixation devices, which are by itself inducers of adhesion formation.

The mesh implant can be attached to said tissue by any known means, including by mechanical fixation devices. Said antiadhesive barrier can also cover said mechanical fixation device. Such mechanical fixation devices are e.g. sutures, tacks, (endo)anchors or staples. Depending on the size of the mesh implant it is also conceivable that the mesh implant itself is fixed by a biocompatible adhesive, such as a fibrin sealant as disclosed above. After the mesh implant is fixed onto the tissue, the antiadhesive barrier is applied onto the mesh. It is also possible to apply the antiadhesive barrier onto the mesh simultaneous with the fixation of the mesh onto the tissue. In particular preferred embodiments the antiadhesive barrier is sealed to the mesh with the biocompatible adhesive. The biocompatible adhesive can be applied onto the antiadhesive barrier by e.g. spraying. The application (of the adhesive but also the mesh and barrier) can be through an open incision or by laparoscopy. It is possible to place the mesh in onlay, inlay, sublay, but in particular by intraperitoneal onlay mesh technique.

Furthermore the invention relates to a mesh implant, antiadhesive barrier and a biocompatible adhesive, respectively, for use in any inventive method. In this aspect the use of a mesh implant or antiadhesive barrier for the manufacture of a surgical device is included for any method, as well as the use of the biocompatible adhesive for the manufacture of a pharmaceutical preparation for any inventive method. To be used in a surgical method these products are preferably sterile.

In another aspect the present invention relates to a kit comprising an antiadhesive barrier and a biocompatible adhesive, optionally a mesh implant, and instructions for its use. The kit may be used for any inventive method, in particular a method of fixating a mesh implant to a tissue of a subject comprising attaching said mesh implant to said tissue, covering said mesh implant by an antiadhesive barrier, wherein said antiadhesive barrier is attached to said mesh implant by a biocompatible adhesive, and instructions for said method. This method may be any method or embodiment as described herein.

In another aspect the present invention relates to the use of a biocompatible adhesive for fixating a mesh implant to a tissue of a subject comprising attaching said mesh implant to said tissue, covering said mesh implant by an antiadhesive barrier, wherein said antiadhesive barrier is attached to said mesh implant by a biocompatible adhesive.

The present invention is further exemplified by the following examples without being limited thereto.

The following abbreviations are used:
AM amniotic membrane
BW body weight
FS fibrin sealant
ip intraperitoneal
sc subcutaneous
VM Vitamesh®

EXAMPLES

Example 1

Use of an Anionic Polysaccharide

Male Sprague Dawley rats, weighing 400-500 g are used. A macroporous, middleweight polypropylene mesh is used in the trial. This mesh should not be used intraabdominally without antiadhesive barriers. Polypropylene mesh only serves as control group.

The antiadhesive barrier tested in combination with VM consists of anionic polysaccharides (Seprafilm®). The choice of the antiadhesive barrier is based on experimental and clinical studies showing an antiadhesive effect and good biocompatibility of the materials as well as on their availability to be purchased separately.

Observation time is 30 days to assure completed wound healing in order to be able to examine tissue integration and long-term complications like seroma and adhesion formation. Surgery is performed under sterile conditions.

Rats are anaesthetized with an ip injection of 110 mg/kg BW of Ketavet® (Ketamine-hydrochloride 100 mg/ml, Pharmacia, Germany) and 12 mg/kg BW of Rompun® (Xylazine-Hydrochloride, Bayer, Germany) and receive an sc injection of 0.07 ml/400 g BW of Butomidor® (Butorphanol, Richter Pharma, Austria) preoperatively to reduce visceral pain.

The belly is thoroughly shaved and skin disinfection is performed. Subsequently, the skin is incised with a scalpel and the subcutaneous fat tissue is bluntly detached from the abdominal muscles. A transverse U-shaped laparotomy is made in the upper third of the abdomen, beginning and ending about 1.5 cm above the inguinal region. The abdominal wall is flipped caudally, exposing the peritoneum and allowing a clear view on the implant site. This model has been described previously (Petter-Puchner et al., J. Surg. Res. 150(2)(2008): 190-195).

One mesh per animal (VM 2×2 cm) is placed on the peritoneum in a midline position. A distance of at least 1 cm from the laparotomy wound is ensured. VM is fixed with 4 non-resorbable sutures (Synthofil® 4/0, Ethicon, Germany) to the abdominal wall. An antiadhesive barrier of 2.5×2.5 cm is placed on the visceral side of the implant and fixed to the mesh with FS (Artiss®, a slow solidifying version of Tisseel, Baxter Bioscience, Austria). The mesh and the peritoneum within 2 mm of the implant were covered with 0.2 ml of FS and according to randomization a patch of Seprafilm® is placed on this area. FS is applied with the EasySpray® system (Baxter Bioscience, Vienna). The spray application allows the delivery of an equally thin layer of FS. The antiadhesive barrier size of 2.5×2.5 cm provides sufficient overlap of mesh borders as well as sutures. To assure full FS polymerization the abdominal flap is closed not before 5 minutes after antiadhesive barrier placement. Meshes and sutures are not covered in the control group. The skin incision is closed in anatomical layers and 1 ml of physiological saline as well as 0.07 ml/400 g BW of Metacam® (Meloxicam, Boehringer Ingelheim, Germany) is administered sc.

Analgesic treatment is routinely supplied once daily for 3 days postoperatively by sc application of Metacam® 0.07 ml/400 g BW. Animals are checked daily for signs of infection, seroma- or abscess formation.

Rats are sacrificed in deep anaesthesia and preoperative analgesia 30 days postoperative by an intracardial injection of 1 ml of Thiopental® (Sandoz, Austria). The scoring of adhesion formation, tissue integration, seroma formation and inflammation are performed post mortem.

Example 2

Use of a Collagen Membrane

The setup is the one as described in Example 1, but the antiadhesive barrier tested in combination with VM consists of atelocollagen type 1 (Prevadh®).

Example 3

Use of Amniotic Membrane

Besides the various commercially available antiadhesive barriers which are specifically designed for the combination with synthetic hernia meshes, preliminary findings indicate a potential of sealed AM for this indication. Due to the biomechanical characteristics of AM, the technical difficulties concerning application to the mesh and fixation are similar to the use of other organic barriers and coatings.

The efficacy of FS to securely fit and fix AM to a polypropylene mesh in our previously published IPOM model in rats (n=14). The AM is checked for vitality prior to implantation and pre-cut to squares of 2×2 cm. These samples are attached to VM by means of 0.2 ml Artiss (4 I.U.) each. The mesh is additionally fixated with 4 corner sutures.

Antiadhesive properties of AM are shown and AM is securely attached to the mesh after an observation period of 14 days. FS is fully degraded and neovascularisation is detected histologically. Our preliminary findings suggest that vital AM might be more susceptible to rapid integration into the abdominal wall than other barriers tested.

The advantages of the FS fixation to the mesh include the preservation of the integrity of AM, an enhanced integration of the mesh and a rapid incorporation of AM as well as the reduction of perforating fixation devices.

Parameter Evaluation

Adhesion formation as well as tissue integration, seroma formation and inflammation are evaluated. Each mesh is scored by two investigators unaware of the randomisation at evaluation. In case of discrepancies between observers the worse score is accepted. The scores using an A (no), B (modest) to C (severe alteration) scale have previously been reported in studies on biomeshes and synthetic meshes (Petter-Puchner et al., J. Surg. Res. supra (2008)).

Percental Adhesion-Coverage of Mesh Surface (PAM):

is gathered by evaluating the percentage of adhesion-covered mesh surface in situ by placing a grid of 2×2 cm side length and 16 squares of 0.0625 $cm^2$ each over the mesh and counting the number of squares covering adhesions. Burger et al. have considered this method appropriate in an experimental study on eight different meshes for ventral hernia repair. (Burger et al., Surg Endosc 20 (2006): 1320-1325).

Statistical Analysis

To check for differences between the groups an analysis of variances (ANOVA) is performed of the outcome parameters. For ANOVA "score results" are used as dependent variable and "group" serve as independent factor. Post-hoc pair wise comparisons are performed by the method of Tukey in order to identify the groups showing statistically different results. A p-value $p<0.05$ is considered to indicate statistical significance.

DISCUSSION

A growing body of literature exists about the main complications related to IPOM, e.g. adhesion and seroma formation, impaired functionality and chronic pain. Among the continuously newly released products to target these problems antiadhesive barriers are produced to cover synthetic meshes and fixation devices in the intraabdominal position to shield the mesh from direct contact with intraabdominal organs.

The present invention provides an evaluation of the efficacy and safety of a new antiadhesive barrier-fixation technique: the atraumatic fixation of antiadhesive barrier to the mesh using FS, which is successfully used for mesh fixation in inguinal and incisional hernia repair. Previously sutures or tacks were required to attach an antiadhesive barrier to the mesh. These devices provide a punctual fixation of the antiadhesive barrier with the risk of herniation of bowel loops between antiadhesive barrier and mesh as well as the risk of cutting through the antiadhesive matrices. The intraoperative handling of FS is convenient. Antiadhesive barriers are attached to mesh and peritoneum. Although most of the antiadhesive barriers had dissolved at the time of evaluation, our results show a significant antiadhesive effect in 2 of 3 treatment groups. Surprisingly, FS is an excellent option to safely keep antiadhesive barriers in place by creating a 3-dimensional contact area between antiadhesive barrier, mesh and fixation devices. Furthermore, the FS fixation of antiadhesive barriers allows the coverage of "hot spots" for adhesion formation, e.g. sutures, tacks and mesh margins, what presents a distinct advantage to perforating fixation devices, protruding into the abdominal cavity. Macroscopical and histological results underline the safety of the technique by the lack of seroma or infection and the moderate inflammatory response.

Furthermore, the invention illustrates the antiadhesive efficacy and tissue integration of different antiadhesive barriers in combination with a polypropylene mesh, which is used as an example, but other porous meshes are equally suited. The antiadhesive barriers tested differ substantially in terms of degradation times, handling properties and costs.

Concerning adhesion prevention, the good results in terms of antiadhesive efficacy are achieved. Consulting literature the antiadhesive effect of antiadhesive barriers seems to be most efficient until wound healing is completed. For peritoneal defects time of healing has been shown to be approximately 10 days.

Concerning the secondary outcome parameters there is no seroma observed in this trial, which could be explained by the lack of a large hernia sac as well as by the use of FS, which is a potent agent in the prevention of seroma formation in IPOM repair. No undesirable inflammation occurs at the implant site and a moderate foreign body reaction is seen in histological examination.

In conclusion, it was surprisingly found that biocompatible adhesives, such as FS, are excellent agents for antiadhesive barrier fixation. The attachment of antiadhesive barriers to a macroporous mesh by the means of FS allows a 3 dimensional coverage of the whole implant and all kinds of fixation devices (including tacks and anchors.

The invention claimed is:

1. A method of fixating a mesh implant to a tissue of a subject comprising attaching said mesh implant to said tissue, covering said mesh implant by an antiadhesive barrier, wherein said antiadhesive barrier is attached to said mesh implant by a biocompatible adhesive that is applied onto said antiadhesive barrier by spraying, in an open incision or by laparoscopy, wherein said biocompatible adhesive comprises at least two components, which are either premixed and applied or mixed upon application.

2. The method of claim 1, wherein said antiadhesive barrier is a foil or membrane.

3. The method of claim 1, wherein said antiadhesive barrier comprises a biopolymer, a polysaccharide, hyaluronic acid, cellulose, cellulose, a cellulose derivative, polylactic acid, poly(L-lactide-co-D,L-lactide), type-1 atelocollagen, collagen, poly(lactic-co-glycolic acid), polyglactin or mixtures thereof or a natural biologic membrane like amnion, small intestinal submucosa, skin or mixtures thereof or a non-resorbable biocompatible membrane.

4. The method of claim 1, wherein said biocompatible adhesive comprises natural polymers, fibrinogen and/or thrombin.

5. The method of claim 1, wherein the antiadhesive barrier is applied onto said mesh simultaneous with the attaching of the mesh onto said tissue.

6. The method of claim 1, wherein the biocompatible adhesive holds the antiadhesive barrier in place for at least fourteen days before biodegrading.

7. The method of claim 1, wherein two of the at least two components comprising the biocompatible adhesive are fibrinogen and thrombin.

8. The method according to claim 1, wherein the mesh implant is placed on a peritoneum of the patient, such that the mesh implant is disposed between an abdominal wall of the patient and an intraperitoneal organ of the patient.

9. The method according to claim 1, wherein the mesh implant is placed intraperitoneally within the patient.

10. The method according to claim 1, wherein the patient has an abdominal wall defect, and the mesh implant is placed between the abdominal wall defect and an intraperitoneal organ of the patient.

11. The method according to claim 1, wherein the patient has a hernia defect, and the mesh implant is placed between the hernia defect and an intraperitoneal organ of the patient.

12. The method according to claim 1, wherein said biocompatible adhesive is applied onto said antiadhesive barrier in an open incision.

13. The method according to claim 1, wherein, said biocompatible adhesive is applied onto said antiadhesive barrier by laparoscopy.

14. A method of reducing the risk of adhesion formation after surgery to a mesh implant in a subject comprising attaching said mesh implant to a tissue of the subject, wherein the mesh implant is attached to said tissue by a mechanical fixation device, and covering said mesh implant by a sealed antiadhesive barrier, wherein said antiadhesive barrier is attached to said mesh implant by a biocompatible adhesive that is applied onto said antiadhesive barrier by spraying, in an open incision or by laparoscopy, wherein the antiadhesive barrier also covers said mechanical fixation device such that the mechanical device is not exposed to any other tissue, and whereby said risk is reduced.

15. The method of claim 14, wherein the antiadhesive barrier is attached to the mesh implant by a biocompatible adhesive, and wherein the biocompatible adhesive comprises fibrinogen and thrombin.

16. The method according to claim 14, wherein the mesh implant is placed on a peritoneum of the patient, such that the mesh implant is disposed between an abdominal wall of the patient and an intraperitoneal organ of the patient.

17. The method according to claim 14, wherein the mesh implant is placed intraperitoneally within the patient.

18. The method according to claim 14, wherein the patient has an abdominal wall defect, and the mesh implant is placed between the abdominal wall defect and an intraperitoneal organ of the patient.

* * * * *